United States Patent
Zhang et al.

(10) Patent No.: US 8,816,127 B2
(45) Date of Patent: Aug. 26, 2014

(54) CARBOXYLATION OF TERMINAL ALKYNES

(75) Inventors: Yugen Zhang, Singapore (SG); Dingyi Yu, Singapore (SG)

(73) Assignee: Agency for Science Technology and Research, Singapore (SG)

( * ) Notice: Subject to any disclaimer, the term of this patent is extended or adjusted under 35 U.S.C. 154(b) by 40 days.

(21) Appl. No.: 13/516,425

(22) PCT Filed: Dec. 16, 2010

(86) PCT No.: PCT/SG2010/000475
§ 371 (c)(1),
(2), (4) Date: Aug. 7, 2012

(87) PCT Pub. No.: WO2011/075087
PCT Pub. Date: Jun. 23, 2011

(65) Prior Publication Data
US 2012/0323038 A1 Dec. 20, 2012

(30) Foreign Application Priority Data
Dec. 17, 2009 (SG) .............................. 200908404-7

(51) Int. Cl.
*C07C 51/15* (2006.01)

(52) U.S. Cl.
USPC .......................................... 562/423

(58) Field of Classification Search
None
See application file for complete search history.

(56) References Cited

PUBLICATIONS

Koster et al Eur. J. Org. Chem. 2001, 2507-2511.*
Tsuda et al. Inorganic Chemistry, vol. 15, No. 10, 1976, 2329-2332.*
Jurkauskas et al. Org. Lett, 2003, 5, 2417-2420.*
Sirokman "(N-Heterocyclic-Carbene)-Copper(I) Catalyzed Carbon-Carbon Bond Formation Using Carbon Dioxide" doctoral dissertation, MIT, 2007.*

* cited by examiner

*Primary Examiner* — Brandon Fetterolf
*Assistant Examiner* — Ana Z Muresan
(74) *Attorney, Agent, or Firm* — Conley Rose, P.C.

(57) ABSTRACT

The present invention describes a process for converting a terminal alkyne into an alkynoic acid. In this process the alkyne is exposed to carbon dioxide in the presence of a copper (I) species, a base and a complexing agent capable of complexing copper (I).

20 Claims, 1 Drawing Sheet

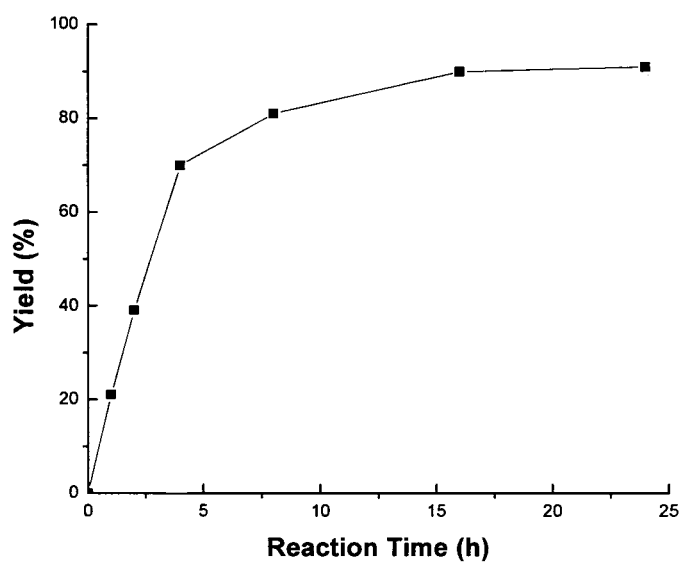

CARBOXYLATION OF TERMINAL ALKYNES

TECHNICAL FIELD

The present invention relates to a carboxylation of terminal alkynes.

INCORPORATION BY CROSS-REFERENCE

This application claims priority from Singapore Patent Application No. 200908404-7 filed on 17 Dec. 2009, the entire contents of which are incorporated herein by cross-reference.

BACKGROUND OF THE INVENTION

The chemical fixation and transformation of carbon dioxide ($CO_2$) has attracted much attention in view of environmental problems, legal and social issues in the past decades. Carbon dioxide is an attractive C1 building block in organic synthesis as it is an abundant, renewable carbon source and an environmentally friendly chemical reagent. The utilization, as opposed to storage, of $CO_2$ is indeed more attractive especially if the conversion process to useful bulk products is an economical one. Unfortunately, carbon dioxide is a highly oxidized and thermodynamically stable compound, and is consequently not very reactive. Significant efforts have been devoted towards exploring technologies for $CO_2$ transformation, however harsh and severe reaction conditions are one of the major limitation for their practical applications. Therefore, the development of efficient catalyst systems for $CO_2$ utilization under mild conditions is highly desired, especially for real world applications.

Carboxylic acids are one of the most important types of compounds in medicinal chemistry and also in fine chemicals synthesis. Although there are many well-established protocols for the preparation of carboxylic acids, the direct carboxylation of carbon nucleophiles using $CO_2$ as the electrophile is the most attractive and straightforward method. While the formation of a stable C—C bond is desired for $CO_2$ fixation, its reality remains hitherto unaccomplished, and remains the most challenging aspect thus far. Typically, this type of reactions is facilitated by the insertion of $CO_2$ into a metal-carbon bond, as shown in Scheme 1.

Scheme 1: Insertion of $CO_2$ in a carbon-metal bond

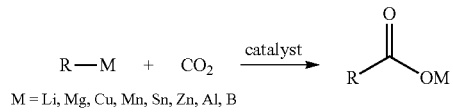

M = Li, Mg, Cu, Mn, Sn, Zn, Al, B

Recently, this protocol was expanded to less reactive organometallic reagents where catalytic insertion $CO_2$ into less polarized metal-carbon bonds (C—Sn, C—Zn, C—B) with high chemoselectivity and under mild reaction conditions was achieved. Generally, such reactions take place under mild reaction conditions. However widespread use of these methods is limited by the synthesis of related organometallic reagents as precursors and the restricted substrate scope. In the past decades, several interesting systems have been reported for metal mediated reductive carboxylation of alkenes and alkylenes with $CO_2$ to form carboxylic acids or esters. However, most of those systems need either stoichiometric amount of transition metals as reactants or excess amount of organometallic reagents for transmetallation processes. The development of catalytic systems for synthesis of carboxylic acid product by direct $CO_2$ carboxylation without using stoichiometric organometallic reagents is highly desired, especially for commercial applications. An alternative possibility to achieve the catalytic synthesis carboxylic acid from $CO_2$ is by direct C—H bond activation and carboxylation, but unfortunately, this is still an undeveloped field.

Previously known methods for the preparation of alkynyl carboxylic acids include $CO_2$ insertion into metal-carbon bond of organometallic reagents, hydrolysis of bromide and related derivatives and the oxidation of preoxidized substrates, such as alcohols or aldehydes. Despite the efficiency of these conventional procedures, they are restricted by the severe reaction conditions and the organometallic reagent that dramatically limited the synthesis and application of a wide scope of functionalized propiolic acids.

OBJECT OF THE INVENTION

It is the object of the present invention to substantially overcome or at least ameliorate one or more of the above disadvantages.

SUMMARY OF THE INVENTION

In a first aspect of the invention there is provided a process for converting a terminal alkyne into an alkynoic acid comprising exposing the alkyne to carbon dioxide in the presence of a copper(I) species, a base and a complexing agent capable of complexing copper(I).

The following options may be used in conjunction with the first aspect, either individually or in any suitable combination.

The copper(I) species may be a copper(I) halide, e.g. copper (I) chloride. It may be present in catalytic amount relative to the terminal alkyne. It may be present at less than about 10 mol % relative to the terminal alkyne, or less than about 5 or 2 mol %, or at about 1 to about 10 mol %, or at about 1 to 5, 1 to 2, 2 to 10, 5 to 10 or 2 to 5 mol %, e.g. about 1, 2, 3, 4, 5, 6, 7, 8, 9 or 10 mol %.

The base may be a basic salt. It may be a basic inorganic salt. It may be a carbonate or a phosphate or an acetate. It may be an alkoxide. It may be for example a t-butoxide such as potassium t-butoxide. It may be a Group I metal basic salt. It may be a Group II metal basic salt. It may be for example sodium carbonate, sodium acetate, potassium phosphate, potassium carbonate or it may be caesium carbonate. Alternatively organic bases such as nitrogen containing bases may be used. Examples of such nitrogen containing bases include DBU (diazabicycloundecene) and DBN (diazabicyclononene). The base may be present at a concentration of at least about 10 mol % of the terminal alkyne, or at least about 20, 50, 80 or 100 mol %, or about 10 to about 200 mol %, or about 10 to 100, 10 to 50, 50 to 200, 100 to 200 or 80 to 120 mol %, e.g. about 10, 20, 30, 40, 50, 60, 70, 80, 90, 100, 110, 120, 130, 140, 150, 160, 170, 180, 190 or 200 mol % or, in some instances, more than 200 mol %.

The complexing agent may be an organic nitrogen species. It may have at least two nitrogen atoms per molecule. In this case the two nitrogen atoms may be disposed in the complexing agent so as to be capable of complexing the organic nitrogen species. It may be a diaminoalkane, e.g. ethylenediamine, dialkyl (e.g. dimethyl)ethylenediamine, tetraalkyl (e.g. tetramethyl)ethylenediamine etc. It may be a bis-tertiary amino alkane or a bis-secondary amino alkane or a bis-primary amino alkane. It may be an α,ω-diaminoalkane, in which each amine group may be primary, secondary or tertiary. The alkane portion of these diaminoalkanes may be C2 to C12 or more than C12, or may be C2 to C6, C6 to C12 or C2 to C4 (e.g. C2, C3, C4, C5, C6, C7, C8, C9, C10, C11 or C12) and may (except for C2) be linear, branched or cyclic. The complexing agent may comprise a nitrogen heterocycle. It may comprise a heterocyclic system comprising two or more than two nitrogen atoms, wherein two of the nitrogen atoms are disposed so as to be capable of complexing the copper (I). the complexing agent may for example comprise a bis-pyridine (e.g. 2,2'-bispyridine) or a terpyridine (e.g. a 2,2':6',2''-terpyridine) or a phenanthroline (e.g. a 1,10-phenanthroline), each being optionally substituted.

In some instances the complexing agent is an N-heterocyclic carbene, optionally an N-heterocyclic carbene bearing one or more (e.g. 2 or 3) bulky substituents such as optionally substituted aromatic and/or heteroaromatic groups. The complexing agent may be a poly-N-heterocyclic carbene, e.g. a polyimidazolium. In some instances may be a monomeric N-heterocyclic carbene (e.g. a monomeric N,N'-disubstituted imidazolium), or a dimeric, trimeric or oligomeric N-heterocyclic carbene (e.g. a dimeric, trimeric or oligomeric imidazolium). The N-heterocyclic carbene may be for example IMes (N,N'dimesitylimidazolium) or N,N'-bis(2,6-dimethylphenyl)imidazolium. It may be a stable N-heterocyclic carbene. It may be stable under the conditions of temperature and solvent used in the process of the invention. The N-heterocyclic carbene may be generated by reaction of the corresponding N-heterocyclic (optionally poly-N-heterocyclic) salt (e.g. an imidazolium or a polyimidazolium salt) with a base. This is described for example in PCT/SG2006/000187 (WO/2007/114793), the contents of which are incorporated herein by cross reference. The copper(I) species and the complexing agent may be in the same molecule. In this case the complexing agent is a poly-N-heterocyclic carbene in which at least some carbene centres are complexed with copper(I). In this case process may comprise the step of complexing the carbon dioxide with the complexing agent to form a polymeric reagent comprising a poly-N-heterocyclic carbene in which some carbene centres are complexed with copper(I) and other carbene centres are complexed with carbon dioxide. This step may be conducted before exposing the alkyne to said polymeric reagent so that the complexed carbon dioxide can react with the alkyne to form the carboxylic acid. In the polymeric reagent described above, the ratio of copper(I) complexed carbene centres to carbon dioxide complexed carbene centres may be about 2:1 to about 1:2, or about 1.5:1 to 1:1.5, 1.2:1 to 1:1.2, 2:1 to 1:1, 1.5:1 to 1:1, 1.2:1 to 1:1, 1:1 to 1:1.2, 1:1 to 1:1.5 or 1:1 to 1:2, e.g. about 2:1, 1.5:1, 1.2:1, 1:1, 1:1.2, 1:1.5 or 1:2. The carbene centres may be substantially all complexed (either with copper(I) or with carbon dioxide) or about 90, 80, 70, 60 or 50% of them may be complexed with one or other of these.

The complexing agent may be present in a catalytic amount. It may be used in an amount of less than about 10 mol % relative to the alkyne, or less than about 5 or 2 mol %, or at about 1 to about 10 mol %, or at about 1 to 5, 1 to 2, 2 to 10, 5 to 10 or 2 to 5 mol %, e.g. about 1, 1.5, 2, 2.5, 3, 3.5, 4, 4.5, 5, 6, 7, 8, 9 or 10 mol %. It may be present in an approximately equimolar amount relative to the copper(I) species, or may be present in greater than equimolar amount relative to the copper(I) species. It may be present in a molar ratio to the copper (I) species of about 1.1, 1.2, 1.3, 1.4, 1.5, 1.6, 1.7, 1.8, 1.9 or 2 or more than 2. In some instranes it may be present in less than equimolar amount relative to the copper(I) species. In cases in which (as described above) a polymeric reagent comprising complexed copper and complexed carbon dioxide is used, the polymeric reagent may be used in an equimolar or greater amount with respect to the alkyne, e.g. at a level of at least about 100, 120, 150 or 200 mol %, or about 100 to about 200 mol %, or about 100 to 150, 150 to 200, 110 to 150 or 120 to 170 mol %, e.g. about 100, 110, 120, 130, 140, 150, 160, 170, 180, 190 or 200 mol %, although lower amounts (e.g. about 50 to 100%) may be used, resulting generally in a lower yield of product.

The process may be conducted at ambient temperature. It may be conducted at about 15 to about 30° C., or about 15 to 20, 20 to 25 or 25 to 30° C., e.g. about 15, 20, 25 or 30° C. The partial pressure of carbon dioxide over the reaction may be about 1 atmosphere or less, e.g. about 0.5 to about 1 atmosphere, e.g. about 0.5, 0.6, 0.7, 0.8, 0.9 or 1 atmosphere. In some cases the reaction may be conducted at higher partial pressures, e.g. up to about 2, 3, 4, 5 or 10 atmospheres, or about 1 to about 10 atmospheres or about 1 to 5, 1 to 2, 2 to 10, 5 to 10 or 2 to 5 atmospheres, e.g. about 1, 1.5, 2, 2.5, 3, 3.5, 4, 4.5, 5, 5.5, 6, 6.5, 7, 7.5, 8, 8.5, 9, 9.5 to 10 atmospheres. It may be conducted in an atmosphere of substantially (e.g. at least about 95%, or at least about 99% pure) carbon dioxide, or may be conducted under an atmosphere of carbon dioxide mixed with a diluent. The diluent may be a gas which is inert under the reaction conditions used. It may be for example nitrogen, or argon, or helium or neon or a mixture of any two or more of these. In some instances the carbon dioxide (either pure or with a diluent as described above) may be bubbled through the reaction mixture throughout the reaction. The reaction may be conducted under ambient total pressure, or at about 1 to about 2 atmospheres total pressure.

The process may be conducted for sufficient time to achieve a desired yield, or a desired level of conversion of alkyne to alkynoic acid. The time may depend on the conditions used, in particular the partial pressure of carbon dioxide and the temperature. The time may be at least about 1 hour, or at least about 2, 5, 10, 20 or 50 hours, or may be about 1 to about 100 hours, or about 1 to 50, 1 to 25, 1 to 10, 1 to 5, 5 to 100, 10 to 100, 20 to 100, 50 to 100, 5 to 50, 5 to 20 or 20 to 50 hours, e.g. about 1, 2, 3, 4, 5, 6, 7, 8, 9, 10, 12, 14, 16, 18, 20, 25, 30, 35, 40, 45, 50, 60, 70, 80, 90 or 100 hours, or may be more than 100 hours.

The process may be conducted in a solvent. It may be conducted in a dipolar aprotic solvent. The solvent may be water soluble. It may be for example DMF, DMSO, HMPT or HMPA or a mixture of any two or more of these. It may be conducted in an ionic liquid.

The alkyne may be any suitable alkyne. It may be a deactivated alkyne. It may be for example a 2-phenylalkyne. It may have a $NO_2$, OH, CN, CHO or COOH group or more than one of any one or more of these. It may comprise a mixture of two or more alkynes, whereby the process produces a mixture of alkynoic acids. In the event that the alkyne contains more than one (e.g. 2 or 3) terminal alkyne groups, the process may produce predominantly or exclusively a monocarboxylic acid. By adjusting conditions, in some cases, a dicarboxylic acid may be formed from an alkyne having two terminal alkyne groups. The alkyne may have a carbon atom other than the terminal alkyne carbon atom bonded to the non-terminal alkyne carbon atom. The alkyne may have structure X—C≡C—H, where X is bonded to the C≡C group by a C—C bond.

In an embodiment there is provided a process for converting a terminal alkyne into an alkynoic acid comprising exposing the alkyne in a dipolar aprotic solvent such as DMF to carbon dioxide at about 1 atmosphere pressure and about ambient temperature in the presence of a carbonate salt such as caesium carbonate, a catalytic amount of a copper(I) halide and a catalytic amount of a diaminoalkane.

In another embodiment there is provided a process for converting a terminal alkyne into an alkynoic acid comprising exposing the alkyne in a dipolar aprotic solvent such as DMF to carbon dioxide at about 1 atmosphere pressure and about ambient temperature in the presence of a carbonate salt such as caesium carbonate, a catalytic amount of a copper(I) halide and a catalytic amount of a poly-N-heterocyclic carbene.

In another embodiment there is provided a process for converting a terminal alkyne into an alkynoic acid comprising exposing the alkyne to a poly-N-heterocyclic carbene reagent in which about 50% of carbene sites are complexed with copper(I) and about 50% of carbene sites are complexed with carbon dioxide, said process being conducted at about ambient temperature in a dipolar aprotic solvent such as DMF.

In a second aspect of the invention there is provided a process for converting a terminal alkyne into an alkynoic acid comprising exposing the alkyne to carbon dioxide in the presence of a carbonate salt at a temperature of at least about 60° C. and a partial pressure of carbon dioxide of at least about 1 atmosphere.

The following options may be used in conjunction with the second aspect, either individually or in any suitable combination.

The carbonate salt may be, or may comprise, an alkaline metal carbonate. It may be, or may comprise, caesium carbonate. It may be present in equimolar or greater amount relative to the terminal alkyne. It may be present in a molar excess of about 0, 5, 10, 15, 20, 24, 30, 35, 40, 45 or 50%, optionally more than 50%, over the terminal alkyne.

The partial pressure of carbon dioxide over the reaction may be at least about 1 atmosphere, or at least about 1.5, 2, 2.5, 3, 3.5, 4, 4.5 or 5 atmospheres, or about 1 to about 10 atmospheres, or about 1 to 5, 1 to 2, 2 to 10, 5 to 10 or 2 to 5 atmospheres, e.g. at about 1, 1.5, 2, 2.5, 3, 3.5, 4, 4.5, 5, 6, 7, 8, 9 or 10 atmospheres. The process may be conducted in an atmosphere of substantially (e.g. at least about 95%, or at least about 99% pure) carbon dioxide, or may be conducted under an atmosphere of carbon dioxide mixed with a diluent. The diluent may be a gas which is inert under the reaction conditions used. It may be for example nitrogen, or argon, or helium or neon or a mixture of any two or more of these.

The process may be conducted in a dipolar aprotic solvent. It may be conducted in a water soluble organic solvent. It may for example be conducted in DMF solvent, or in DMSO, HMPT, HMPA or an ionic liquid, or in a mixture of any two or more of these.

The process may be conducted at about 120 to about 160° C., or about 120 to 140, 140 to 160 or 130 to 150° C., e.g. at about 120, 125, 130, 135, 140, 145, 150, 155 or 160° C. It may be conducted at a temperature sufficiently high to achieve an acceptable rate and/or yield of product and sufficiently low that the product is substantially stable at that temperature, or that the rate of degradation of the product at that temperature is much slower (e.g. at least 2, 3, 4, 5, 6, 7, 8, 9 or 10 times slower) than its rate of production at that temperature.

The process may be conducted for sufficient time to achieve a desired yield, or a desired level of conversion of alkyne to alkynoic acid. The time may depend on the conditions used, in particular the partial pressure of carbon dioxide and the temperature. The time may be at least about 1 hour, or at least about 2, 5, 10, 20 or 50 hours, or may be about 1 to about 100 hours, or about 1 to 50, 1 to 25, 1 to 10, 1 to 5, 5 to 100, 10 to 100, 20 to 100, 50 to 100, 5 to 50, 5 to 20 or 20 to 50 hours, e.g. about 1, 2, 3, 4, 5, 6, 7, 8, 9, 10, 12, 14, 16, 18, 20, 25, 30, 35, 40, 45, 50, 60, 70, 80, 90 or 100 hours, or may be more than 100 hours.

The alkyne may be any of the alkynes described in the first aspect, above. The alkyne may be a 2-phenylalkyne.

The process may be conducted in the absence of copper(I). It may be conducted in the absence of copper.

In an embodiment there is provided a process for converting a terminal alkyne into an alkynoic acid comprising exposing the alkyne to carbon dioxide in the presence of caesium carbonate at a temperature of about 120 to about 160° C. and a partial pressure of carbon dioxide of at least about 2 atmospheres.

BRIEF DESCRIPTION OF THE DRAWING

Embodiments of the present invention will now be described, by way of example only, with reference to the accompanying drawing wherein FIG. 1 is a graph showing the kinetics of copper catalyzed carboxylation of 1a with $CO_2$.

DETAILED DESCRIPTION OF THE PREFERRED EMBODIMENTS

The present invention relates to a copper-catalyzed transformation of $CO_2$ to alkynyl carboxylic acids. The process involves C—H bond activation and carboxylation of terminal alkynes. Compared to the prior art, the present approach is attractive for its mild reaction conditions, simple operation, low cost and tolerance to a wide range of substrates.

The products of the transformation are of general structure X—C≡C—$CO_2$H, where X may be a wide range of monovalent substituents (e.g. optionally substituted aryl, optionally substituted heteroaryl, optionally substituted alkyl, optionally substituted cycloalkyl etc.). These are at times referred to as "alkynyl carboxylic acids", "alkynoic acids", "propynoic acids" or "propiolic acids". In some cases these compounds may be produced in the form of a salt (e.g. a sodium or potassium salt). Unless it is clear from the context that this is not the case, the above terms are intended to incorporate reference to salts thereof.

The ubiquity of alkynyl carboxylic acids in a vast array of medicinally important compounds as well as the tremendous utility as a synthon in organic synthesis makes them particularly attractive targets for pharmaceutical, fine-chemical as well as conductive polymer synthesis. A plethora of well-established methods for the preparation of alkynyl carboxylic acids includes $CO_2$ insertion into metal-carbon bond of organometallic reagents, the well-known hydrosis of bromide and related derivatives, and the oxidation of preoxidized substrates, such as alcohols or aldehydes, Scheme 2A, B and C. Despite the efficiency of these conventional procedures, a major drawback of them is the severe reaction conditions and restrictions of organometallic reagent that dramatically limit the synthesis of a wide scope of functionalized propiolic acids. Therefore, the tolerant and straightforward method for accessing alkynyl carboxylic acids (scheme 2D), as described in the present specification, is highly desirable and provides new opportunities in organic and pharmaceutical synthesis.

Scheme 2: Protocols for synthesis of substituted propiolic acids.

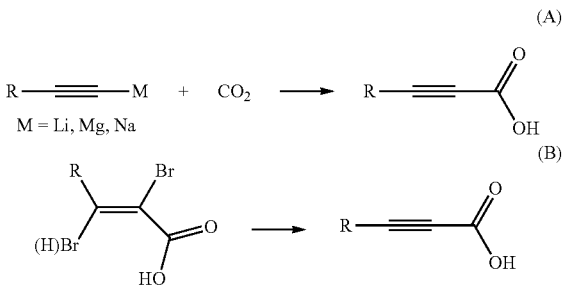

-continued

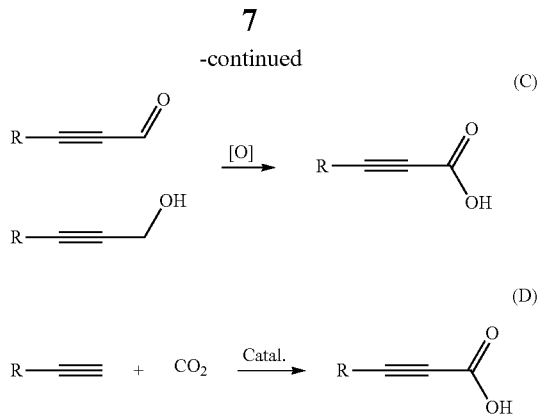

An initial experiment was conducted by using 2 mol % of CuCl, 2 mol % of TMEDA (N,N,N',N'-tetramethylethylenediamine) ligand, and $K_2CO_3$ as base for the carboxylation of 1-ethynylbenzene at ambient temperature and atmospheric pressure. Remarkably, phenylpropiolic acid was produced in excellent yield after acid workup. The isolated pure product was characterized by NMR and elemental analysis. Phenylpropiolic acid was further converted into its methylester and characterized by NMR and GC/MS.

Reaction conditions were optimized by the variation of solvents, ligands, bases and reaction temperature. 1-Ethynylbenzene 1a was taken as an example for the optimization of the reaction conditions. Firstly, the effect of various bases was assayed in the CuCl/TMEDA catalyzed terminal alkynes carboxylation reaction, Table 1.

A control experiment without any base additives was performed. Under this condition 1b was obtained with a yield of merely 55% (Table 1, entry 1). To investigate the influence of the base concentration, the reaction with $K_2CO_3$ as base was chosen as an example. The results indicated that small amounts of base additives promoted the carboxylation reaction. 80% of 1b was isolated when 20 mol % $K_2CO_3$ was added and the product yield was increased to 85% when 60 mol % $K_2CO_3$ was used (Table 1, entries 2 and 3). The yield of 1b reached 90% by further increasing the scale of $K_2CO_3$ to 120 mol % (Table 1, entry 4) and this condition was used in the following studies. The reaction was also carried out with other inorganic bases such as $Na_2CO_3$, NaOAc, $Cs_2CO_3$ and $K_3PO_4$, and 80-92% 1b yields were obtained respectively (Table 1, entries 6-9). Other organic bases such as 2,3,4,6,7,8,9,10-octahydropyrimido[1,2-a]azepine (DBU) and triethylamine ($Et_3N$) were observed to be less effective than inorganic bases. When the carboxylation reaction was run with $Et_3N$ and DBU, the yields of 1b were obtained in 68% and 70%, respectively (Table 1, entries 10, 11). The results clearly demonstrated that the CuCl/TMEDA catalytic system can be used in combination with various bases. The best results were obtained with carbonate salts, such as $K_2CO_3$ and $Cs_2CO_3$ with 90% to 92% 1b yields respectively (Table 1, entries 4, 8). Despite the slightly higher yield obtained with $Cs_2CO_3$, the cheaper base $K_2CO_3$ was chosen for the subsequent experiments.

The effects of the ligand (complexing agent) and catalyst (copper(I) species) loading were studied, Table 2.

TABLE 1

Effect of bases on carboxylation of 1-ethynylbenzene using a CuCl/TMEDA catalytic system with $CO_2$.

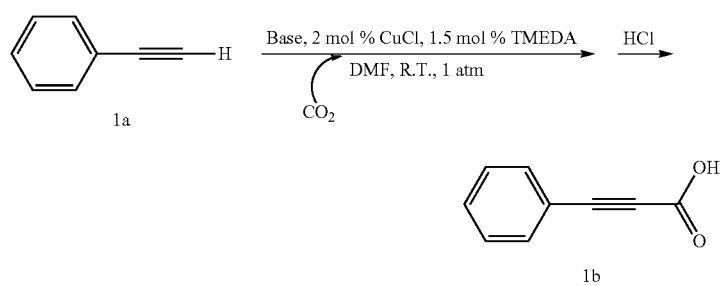

| Entry | Base (mol %). | Reaction Time (h) | Isolated Yields (%) |
| --- | --- | --- | --- |
| 1 | — | 36 | 55 |
| 2 | $K_2CO_3$ (20) | 24 | 80 |
| 3 | $K_2CO_3$ (60) | 18 | 85 |
| 4 | $K_2CO_3$ (120) | 16 | 90 |
| 5 | $K_2CO_3$ (200) | 16 | 92 |
| 6 | $Na_2CO_3$ (120) | 18 | 80 |
| 7 | NaOAc (120) | 18 | 83 |
| 8 | $Cs_2CO_3$ (120) | 16 | 92 |
| 9 | $K_3PO_4$ (120) | 18 | 85 |
| 10 | $Et_3N$ (120) | 24 | 68 |
| 11 | DBU (120) | 24 | 70 |

Reaction conditions: 1a (2.0 mmol), CuCl (2.0 mol %), TMEDA (1.5 mol %), $CO_2$ (1 atm), DMF (4 mL), room temperature

TABLE 2

The variation of ligand and catalyst loading for the carboxylation of 1-ethynylbenzene with $CO_2$.

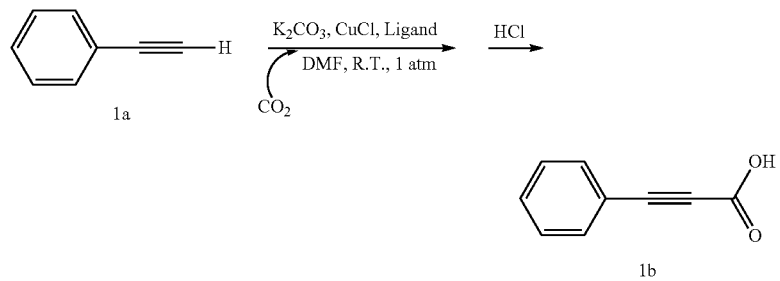

| Entry | Ligand (mol %) | Catalyst (mol %) | Reaction Time (h) | Isolated Yields (%) |
|---|---|---|---|---|
| 1 | — | — | 36 | 0 |
| 2 | TMEDA (0.075) | CuCl (0.1) | 36 | 8 |
| 3 | TMEDA (0.15) | CuCl (0.2) | 36 | 31 |
| 4 | TMEDA (0.4) | CuCl (0.5) | 24 | 85 |
| 5 | TMEDA (0.75) | CuCl (1.0) | 20 | 88 |
| 6 | TMEDA (1.5) | CuCl (2.0) | 16 | 90 |
| 7 | TMEDA (5) | CuCl (5.0) | 14 | 92 |
| 8 | — | CuCl (2.0) | 24 | 50 |
| 9 | DMEDA (1.5) | CuCl (2.0) | 20 | 81 |
| 10 | Imes-NHC (1.5) | CuCl (2.0) | 18 | 68 |
| 11 | Imes-NHC (5) | CuCl (2.0) | 16 | 88 |
| 12 | DBU (1.5) | CuCl (2.0) | 18 | 72 |
| 13 | DBU (5) | CuCl (2.0) | 16 | 86 |

Reaction conditions: 1a (2.0 mmol), CuCl (2.0 mol %), Ligand, $CO_2$ (1 atm), $K_2CO_3$, DMF (4 mL), r.t.

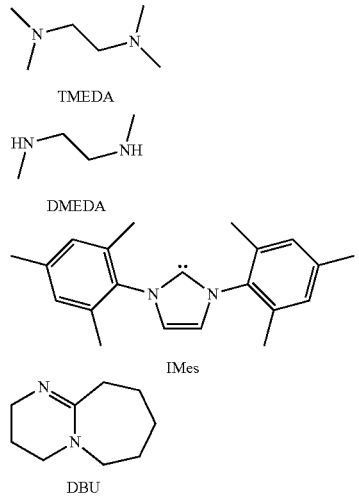

With 2.0 mol % CuCl catalyst in the absence of ligand, the yield of 1b dropped to 50% (Table 2, entry 8). This result indicates that the σ donor ligand can increase the reactivity of the carbanionic intermediate. To identify the most effective ligand, the carboxylation of 1a was run in the presence of 2 mol % CuCl with different ligands, including N,N,N',N'-tetramethylethylenediamine (TMEDA), N,N'-dimethyl-ethanediamine (DMEDA), 1,3-dimesitylimidazol-2-ylidene (IMes), and DBU, see Table 2. It was found TMEDA was the best ligand for the reaction, with 1b yield of 90% (Table 2, entry 6), followed by DMEDA (81%) (Table 2, entry 9), IMes (68%) (Table 2, entry 10) and DBU (72%) (Table 2, entry 12). When the amount of monodentate ligands, IMes and DBU, were increased to 5 mol %, the yields of 1b were also increased up to 86-88% (Table 2, entries 11 and 13).

For the carboxylation of 1-ethynylbenzene 1a, as the catalyst loadings was reduced from 5 mol % to 0.5 mol %, good to excellent yields could still be obtained after prolonged reaction time (Table 2, entry 4-7). The yield of 1b decreased sharply to 8% when the catalyst loading further reduced to 0.1 mol % (Table 2, entry 2). No reaction was observed for the control experiment without copper catalyst (Table 2, entry 1).

However, in the presence of 1.2 mmol $Cs_2CO_3$, without copper catalyst, 1a (1 mmol) was treated with $CO_2$ (2.5 atm) in N,N-dimethylformamide (DMF) at 120° C. for 14 hrs, and subsequent acid hydrolysis afforded 3-phenylpropiolic acid (1b) in excellent yield. Encouraged by this result, the reaction conditions were further investigated. It was found that both the reaction temperature and $CO_2$ pressure are very crucial for this base promoted carboxylation reaction. The optimized reaction temperature range is between 120 to 160° C. In this temperature range, the yield of 1b could reach more than 93% with 2.5 atm of $CO_2$ (entries 11-13, Table 3).

TABLE 3

Effect of pressure and temperature on carboxylation of 1-ethynylbenzene with $CO_2$.[a]

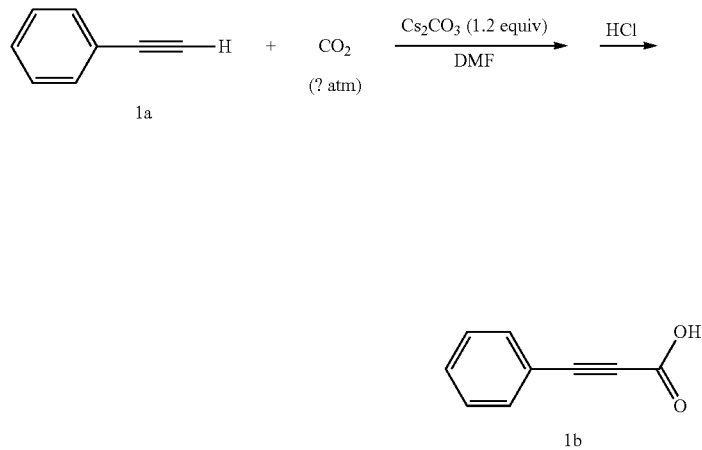

| Entry | Pressure (atm) | Temperature (° C.) | Reaction Time (hours) | Yield of 1b (%) |
|---|---|---|---|---|
| 1[b] | 0 (no $CO_2$) | 120 | 14 | 0 |
| 2 | 1 | 120 | 14 | 20 |
| 3 | 1.5 | 120 | 14 | 60 |
| 4 | 2.5 | 120 | 14 | 95 |
| 5 | 4 | 120 | 14 | 96 |
| 6 | 7 | 120 | 14 | 96 |
| 7 | 2.5 | 25 | 14 | 0 |
| 8 | 2.5 | 60 | 14 | 5 |
| 9 | 2.5 | 80 | 14 | 20 |
| 10 | 2.5 | 100 | 14 | 40 |
| 11 | 2.5 | 120 | 14 | 95 |
| 12 | 2.5 | 140 | 14 | 95 |
| 13 | 2.5 | 160 | 14 | 93 |
| 14 | 2.5 | 180 | 14 | 10 |
| 15 | 2.5 | 200 | 14 | 10 |
| 16 | 7 | 80 | 14 | 30 |

[a]Unless otherwise noted, reaction conditions are as follows: 1-ethynylbenzene (1.0 mmol), $Cs_2CO_3$ (1.2 mmol), $CO_2$, DMF (5 mL), 14 hours.
[b]Reaction was under $N_2$ in absent of $CO_2$.

At lower temperature (60 to 100° C.), the reaction became slow and did not run to completion (entries 8-10, Table 3). A low product yield (30%) was obtained at 80° C. even with over pressured $CO_2$ atmosphere (7 atm) (entry 16, Table 3). There was no reaction observed at room temperature with 2.5 atm $CO_2$ and $Cs_2CO_3$ (entry 7, Table 3). However, as the reaction temperature was raised to over 160° C., the propiolic acid yield dramatically dropped to 10% (entries 14-15, Table 3). This is thought to be because the propiolic acid product 1b is not stable under higher temperature. It may decompose to terminal alkyne 1a through de-carboxylation when it is overheated. When the reaction temperature was fixed at 120° C., it was found that the $CO_2$ pressure was linearly related to the reaction rate. The reaction was completed in 14 hours under 2.5 atm, 7 hours under 4 atm and 3 hours under 7 atm of $CO_2$. Kinetic studies of this reaction showed that 1b was produced approximately linearly with time up to the time where the maximum yield is produced. Entries 1 to 6 of Table 3 show that the yield after 14 hours increases markedly with increasing $CO_2$ pressure, up to a pressure of 2.5 atmospheres. At or above that pressure, the reaction proceeded nearly to completion within 14 hours. A control reaction in the absence of $CO_2$ showed no acid product, suggesting that the COO moiety in the product was not originated from $Cs_2CO_3$ (entry 1, Table 3).

Different solvents were then screened for the copper catalysed reaction, see Table 3a.

TABLE 3a

Effect solvents on carboxylation of 1-ethynylbenzene using a CuCl/TMEDA catalytic System with $CO_2$.

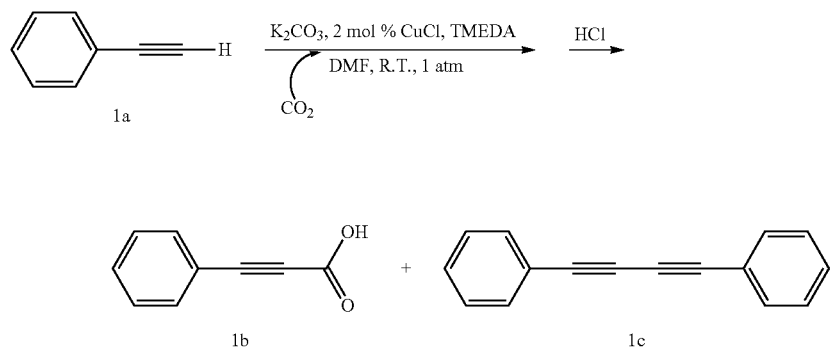

| Entry | Base (mol %) | Solvent | Reaction Time (h) | Isolated yields (%) b | c |
|---|---|---|---|---|---|
| 1 | $K_2CO_3$ (120) | $CH_2Cl_2$ | 36 | 20 | ~4 |
| 2 | $K_2CO_3$ (120) | Toluene | 36 | 14 | ~3 |
| 3 | $K_2CO_3$ (120) | THF | 24 | 78 | ~2 |
| 4 | $K_2CO_3$ (120) | DMSO | 16 | 80 | 0 |
| 5 | $Na_2CO_3$ (120) | $CH_3CN$ | 24 | 60 | 10 |
| 6 | $K_2CO_3$ (120) | $CH_3CN$ | 18 | 75 | ~2 |
| 7 | $Na_2CO_3$ (120) | DMF | 18 | 80 | ~0 |
| 8 | $K_2CO_3$ (120) | DMF | 16 | 90 | ~0 |

Reaction conditions: 1a (2.0 mmol), CuCl (2.0 mol %), TMEDA (1.5 mol %), $CO_2$ (1 atm), $K_2CO_3$ or $Na_2CO_3$, r.t.

The reaction generally worked well in polar solvents and DMF was found to be a good solvent compared with DMSO, THF, $CH_3CN$, toluene and $CH_2Cl_2$. This is thought to be because DMF, a Lewis base, may take the role in the catalyst regeneration step consequently speeding up the reaction. Under the standard condition, a small portion of the dimerization product 1c was obtained in THF, $CH_3CN$, toluene and $CH_2Cl_2$ mediated reaction systems, but did not occur in the DMF and DMSO systems. This result may be due to the high solubility of base and reaction intermediate in the highly polar solvents.

Kinetics studies of this reaction under standard conditions showed that the 1b was formed rapidly in the first 4 hours, reaching a yield of 70%, before the gradual increase to the final yield of 90% in 16 hours. The yield remained constant around 90% even with further increase the reaction time from 16 hours to 24 hours. This is shown in FIG. 1.

With the optimized reaction conditions of 2.0 mol % CuCl, 1.5 mol % TMEDA, 120 mol % $K_2CO_3$ in DMF for 16 hours, the substrate scope of the reaction was studied. The carboxylation of various other terminal alkynes 1-19 with $CO_2$ were carried out smoothly to produce the corresponding propiolic acids in good to excellent yield, see Table 4. Table 5 shows results comparing different complexing agents.

TABLE 4

Copper catalyzed carboxylation of Terminal Alkynes with $CO_2$.[a]

| Entry | Alkynes | Reaction Time (h) | Base | Acid Yields (%, isolated) |
|---|---|---|---|---|
| 1 | PhC≡CH | 16 | $K_2CO_3$ | 90 |
| 2 | 2-methoxyphenyl-C≡CH | 18 | $K_2CO_3$ | 81 |

TABLE 4-continued

Copper catalyzed carboxylation of Terminal Alkynes with $CO_2$.[a]

$$R\text{—}\equiv\text{—}H \xrightarrow[\text{DMF, R.T., 1 atm}]{\text{Base, 2 mol \% CuCl, 1.5\% TMEDA}, CO_2} \xrightarrow{HCl} R\text{—}\equiv\text{—}COOH$$

| Entry | Alkynes | Reaction Time (h) | Base | Acid Yields (%, isolated) |
|---|---|---|---|---|
| 3 | 3-methoxyphenylacetylene | 18 | $K_2CO_3$ | 86 |
| 4 | 4-methoxyphenylacetylene | 18 | $K_2CO_3$ | 89 |
| 5 | 2-fluorophenylacetylene | 16 | $K_2CO_3$ | 80 |
| 6 | 3-fluorophenylacetylene | 16 | $K_2CO_3$ | 85 |
| 7 | 4-fluorophenylacetylene | 16 | $K_2CO_3$ | 88 |
| 8 | 2-chlorophenylacetylene | 16 | $K_2CO_3$ | 84 |
| 9 | 2-chlorophenylacetylene | 16 | $K_2CO_3$ | 86 |
| 10 | 4-chlorophenylacetylene | 16 | $K_2CO_3$ | 86 |
| 11 | 1,3-diethynylbenzene | 24 | $K_2CO_3$ | 90[b] |
| 12 | 4-ethynylbenzaldehyde (OHC-) | 24 | $K_2CO_3$ | (80) |
| 13 | 3-ethynylthiophene | 24 | $K_2CO_3$ | 89 |
| 14 | HO—n-$C_4H_8$—≡ | 24 | $Cs_2CO_3$ | (80) |
| 15 | HOOC—n-$C_4H_8$—≡ | 24 | $Cs_2CO_3$ | (80) |
| 16 | cyclohexylacetylene | 24 | $Cs_2CO_3$ | 91 |
| 17 | Cl—n-$C_4H_8$—≡ | 24 | $Cs_2CO_3$ | 80 |
| 18 | n-$C_4H_8$—≡ | 24 | $Cs_2CO_3$ | 85 |
| 19 | tert-butylacetylene | 24 | $Cs_2CO_3$ | 83 |

[a]Reaction conditions: alkynes (2.0 mmol), CuCl (2.0 mol %), base (2.4 mmol), TMEDA, 1.5 mol %, $CO_2$ (1 atm), DMF (4 mL), r.t.
[b]monocarboxylic acid was obtained.

TABLE 5

Copper catalyzed, carboxylation of terminal alkynes with $CO_2$.[a]

$$R\text{—}\equiv\text{—}H \xrightarrow[\text{DMF, R.T., 1 atm}]{\text{Base, 2-5 mol \% CuCl, Ligand}, CO_2} \xrightarrow{HCl} R\text{—}\equiv\text{—}COOH$$

| Entry | Alkynes | Time (h) | Base | Isolated Yields (%) L1 | L12 |
|---|---|---|---|---|---|
| 1 | phenylacetylene | 16 | $K_2CO_3$ | 90 | 95 |

TABLE 5-continued

Copper catalyzed, carboxylation of terminal alkynes with $CO_2$.[a]

$$R\text{—}\equiv\text{—}H \xrightarrow[\text{DMF, R.T., 1 atm}]{\text{Base, 2-5 mol \% CuCl, Ligand}, CO_2} \xrightarrow{HCl} R\text{—}\equiv\text{—}COOH$$

| Entry | Alkynes | Time (h) | Base | Isolated Yields (%) L1 | L12 |
|---|---|---|---|---|---|
| 2 | 2-methoxyphenylacetylene | 18 | $K_2CO_3$ | 81 | 85 |
| 3 | 3-methoxyphenylacetylene | 18 | $K_2CO_3$ | 86 | 90 |
| 4 | 4-methoxyphenylacetylene | 18 | $K_2CO_3$ | 89 | 92 |
| 5 | 2-fluorophenylacetylene | 16 | $K_2CO_3$ | 80 | 82 |
| 6 | 3-fluorophenylacetylene | 16 | $K_2CO_3$ | 85 | 86 |
| 7 | 4-fluorophenylacetylene | 16 | $K_2CO_3$ | 88 | 86 |
| 8 | 3-chlorophenylacetylene | 16 | $K_2CO_3$ | 84 | 90 |
| 9 | 2-chlorophenylacetylene | 16 | $K_2CO_3$ | 86 | 88 |
| 10 | 4-chlorophenylacetylene | 16 | $K_2CO_3$ | 86 | 90 |
| 11 | 1,3-diethynylbenzene | 24 | $K_2CO_3$ | 90[b] | 90[b] |
| 12 | 3-ethynylthiophene | 24 | $K_2CO_3$ | 89 | 93 |
| 13 | $\equiv\text{—}(CH_2)_4\text{—}\equiv$ | 24 | $Cs_2CO_3$ | 83[b] | 87[b] |
| 14 | $HO\text{—}(CH_2)_4\text{—}\equiv$ | 24 | $Cs_2CO_3$ | 80 | 83 |
| 15 | $NC\text{—}(CH_2)_3\text{—}\equiv$ | 24 | $Cs_2CO_3$ | 82 | 88 |
| 16 | $H_3COOC\text{—}(CH_2)_4\text{—}\equiv$ | 24 | $Cs_2CO_3$ | 82 | 90 |
| 17 | $n\text{-}C_4H_9\text{—}\equiv$ | 24 | $Cs_2CO_3$ | 85 | 85 |
| 18 | tert-butylacetylene | 24 | $Cs_2CO_3$ | 83 | 85 |

L-1: TMEDA; L-12: Poly-NHC

[a]Reaction conditions:
for L1, CuCl (2.0 mol %), TMEDA, 1.5 mol %;
for L12, P(NHC)(NHC—Cu), 5 mol %; alkynes (2.0 mmol), base (2.4 mmol), $CO_2$ (1 atm), DMF (4 mL), r.t.
[b]monocarboxylic acid was obtained.

For aromatic alkynes (1-13) with either electron donating or electron withdrawing groups, the corresponding alkynyl carboxylic acids were obtained in 80-91% yields under standard conditions, respectively. The catalytic system was not sensitive to the type and position of substituents on the benzene ring. The related acid yields of p-, m-, o-substituted 1-ethylbenzene are approximately in the same range. The transformations proceeded smoothly without any side product formation. The initial attempts at the carboxylation of the alkyl-substituted alkynes were unsatisfactory, with a low yield of corresponding acids (~20%). The low reactivity of alkyl-substituted alkynes is probably due to their weak acidity of alkyne proton. It is thought that the large conjugation system comprising the benzene ring and the alkyne C≡C bond in aryl alkynes imposes more negative charge on C1 carbon and make it a stronger nucleophile than in alkyl alkynes, scheme 3.

Scheme 3

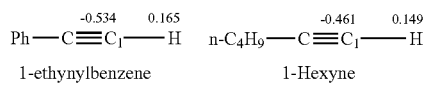

A DFT calculation (B3LYP/6-31G level) indicated that the negative charge on C1 carbon of 1-ethynylbenzene is −0.534 and that of 1-hexyne is −0.461. To investigate, a stronger base, $Cs_2CO_3$ was used instead of $K_2CO_3$, and the yield of corresponding alkyl-substituted propiolic acids was raised to 80-91% (Table 4, entries 14-19).

A remarkable advantage of this mild reaction system is its wide scope of substrate tolerance. The catalytic system is not sensitive to variety functional groups, such as COOH, OH, CHO etc. This provides a powerful tool for synthesis of highly functionalized propiolic acids for the first time.

In general, terminal aromatic alkynes with an electron withdrawing group are deactivated and often inert to many transformations. With an electron withdrawing group on the phenyl ring, the nucleophilicity of C1 carbon of alkynes is reduced dramatically. The carboxylation of 4-nitro-1-ethynylbenzene was unsatisfactory with a very low yield of the corresponding acid (0-8%) under standard conditions. Low yields (around 2%) were also observed as the reaction temperature was adjusted to 0° C. and 50° C. which may be due to the low reaction rate at low temperature and the low stability of reaction intermediate at high temperature. The key step for this transformation is thought to be $CO_2$ insertion into a copper acetylide intermediate. Increasing the nucleophilicity of the carbanionic intermediate may increase the yield of carboxylic acid product. It is well known that N-heterocyclic carbenes (NHC) can activate $CO_2$ in various catalytic transformations. With that in mind, a new NHC—Cu co-catalyst was designed using poly-N-heterocyclic carbene (PNHC) as both ligand and catalyst. PHNC has a three dimensional network structure with carbene units located and fixed in the backbone of the network. Poly(NHC)$_{0.5}$(NHC—Cu)$_{0.5}$ (P1) catalyst was prepared by the reaction of 1 equivalent of CuCl with 2 equivalent of PHNC. In the structure of this catalyst, only half of the carbene species were coordinated with copper with the remainder being free carbenes. The initial experiment was conducted by using 5 mol % of P1 with $Cs_2CO_3$ as base for the carboxylation of 4-nitro-1-ethynylbenzene with $CO_2$ at ambient conditions. Remarkably, 4-nitro-phenylpropiolic acid was produced in 70% yield after acid workup. Good yields were also achieved for terminal aromatic alkynes with other electron withdrawing groups in 36 to 48 hrs (Table 6).

TABLE 6

Cu—NHC (P1) catalyzed carboxylation of deactivated terminal alkynes with $CO_2$.

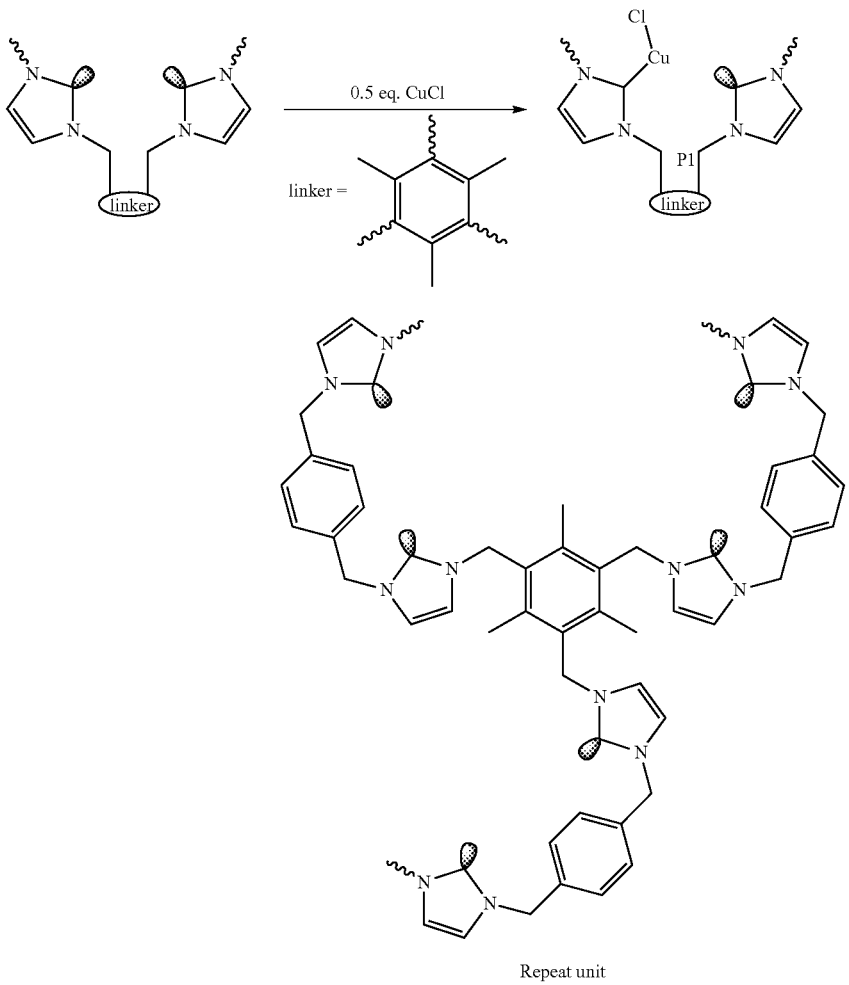

Repeat unit

TABLE 6-continued

Reaction scheme: Ew–C₆H₄–C≡C–H + CO₂ →(Cs₂CO₃, CuCl, Ligand; DMF, R.T., 1 atm) →(HCl) Ew–C₆H₄–C≡C–COOH

| Entry | Alkyne | Time (hrs) | Yields (%) |
|---|---|---|---|
| 1 | O₂N–C₆H₄–C≡CH | 24 | 70 |
| 2 | OHC–C₆H₄–C≡CH | 36 | 68 |
| 3 | NC–C₆H₄–C≡CH | 24 | 72 |
| 4 | HOCH₂–C₆H₄–C≡CH | 36 | 73 |
| 5 | 3-HO–C₆H₄–C≡CH | 36 | 79 |

Reaction conditions: alkynes (2.0 mmol), Cs₂CO₃ (2.4 mmol), P1 (5 mol %), CO₂ (1 atm), DMF (4 mL), r.t.

Table 7 shows the dependence of the reaction on the nature of the complexing agent (ligand) in the process described herein.

TABLE 7

Cu—NHC catalyzed carboxylation of deactivated terminal alkynes with $CO_2$.[a]

Reaction scheme: Ew–C₆H₄–C≡C–H + CO₂ →(Cs₂CO₃, CuCl, Ligand; DMF, R.T., 1 atm) →(HCl) Ew–C₆H₄–C≡C–COOH

| Entry | Alkynes | Ligand (mol %) | CuCl (mol %) | Time (hrs) | Isolated Yields (%) |
|---|---|---|---|---|---|
| 1 | O₂N–C₆H₄–C≡C–H | L1 (10) | 5 | 24 | <5 |
| 2 | " | L2 (10) | 5 | 60 | 2 |
| 3 | " | L3 (10) | 5 | 60 | 3 |
| 4 | " | L4 (10) | 5 | 60 | 8 |
| 5 | " | L5 (10) | 5 | 60 | 5 |
| 6 | " | L6 (10) | 5 | 60 | 9 |
| 7 | " | L7 (10) | 5 | 48 | 21 |

TABLE 7-continued

Cu—NHC catalyzed carboxylation of deactivated terminal alkynes with $CO_2$.[a]

$$Ew\text{—}C_6H_4\text{—}C\equiv C\text{—}H \xrightarrow[CO_2]{Cs_2CO_3, CuCl, Ligand}{DMF, R.T., 1\ atm} \xrightarrow{HCl} Ew\text{—}C_6H_4\text{—}C\equiv C\text{—}COOH$$

| Entry | Alkynes | Ligand (mol %) | CuCl (mol %) | Time (hrs) | Isolated Yields (%) |
|---|---|---|---|---|---|
| 8 | " | L8 (10) | 5 | 48 | 40 |
| 9 | " | L9 (10) | 5 | 48 | 47 |
| 10 | " | L10 (10) | 5 | 48 | 30 |
| 11 | " | L10 (20) | 5 | 48 | 32 |
| 12 | " | L11 (10) | 5 | 48 | 25 |
| 13 | " | L12 (10)[b] | 5 | 48 | 70 |
| 14 | " | L12 (10)[b] | 15 | 48 | 18 |
| 15 | 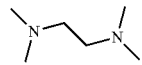 | L12 (10)[b] | 5 | 36 | 68 |
| 16 | 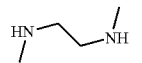 | L12 (10)[b] | 5 | 24 | 72 |
| 17 | 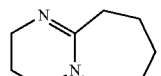 | L12 (10)[b] | 5 | 36 | 73 |
| 18 | 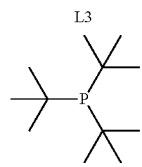 | L12 (10)[b] | 5 | 36 | 79 |

[a]Reaction conditions: alkynes (2.0 mmol), CuCl, $Cs_2CO_3$ (2.4 mmol), ligand, $CO_2$ (1 atm), DMF (4 mL), r.t.
[b]10 mol% of NHC.

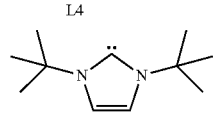

L1

L2

L3

L4

L5

TABLE 7-continued
Cu—NHC catalyzed carboxylation of deactivated terminal alkynes with $CO_2$.[a]
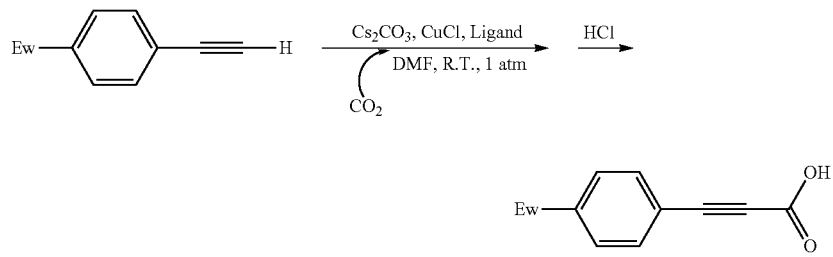
| Entry | Alkynes | Ligand (mol %) | CuCl (mol %) | Time (hrs) | Isolated Yields (%) |
|---|---|---|---|---|---|
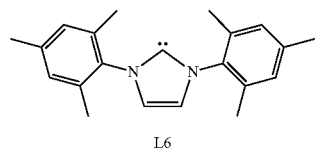
L6
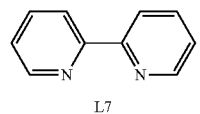
L7
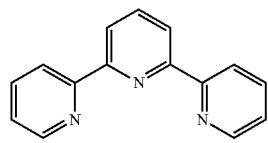
L8
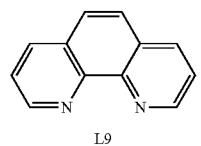 [SMILES: c1cnc2c(c1)ccc1cccnc12]
L9
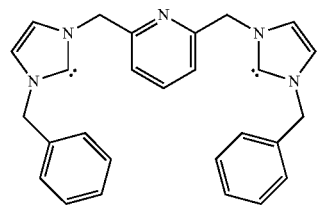
L10
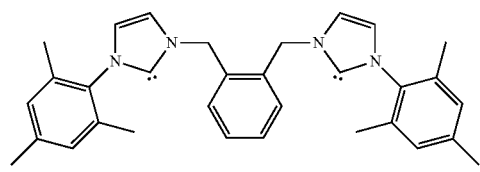
L11

TABLE 7-continued

Cu—NHC catalyzed carboxylation of deactivated terminal alkynes with $CO_2$.[a]

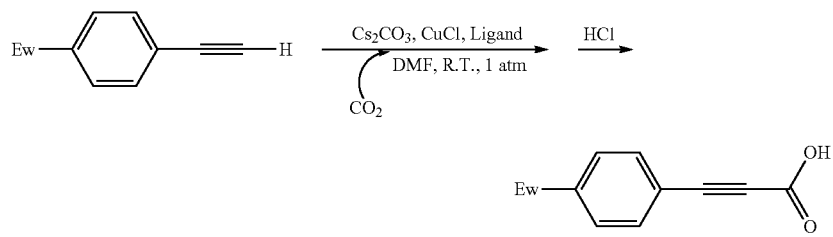

| Entry | Alkynes | Ligand (mol %) | CuCl (mol %) | Time (hrs) | Isolated Yields (%) |
|---|---|---|---|---|---|

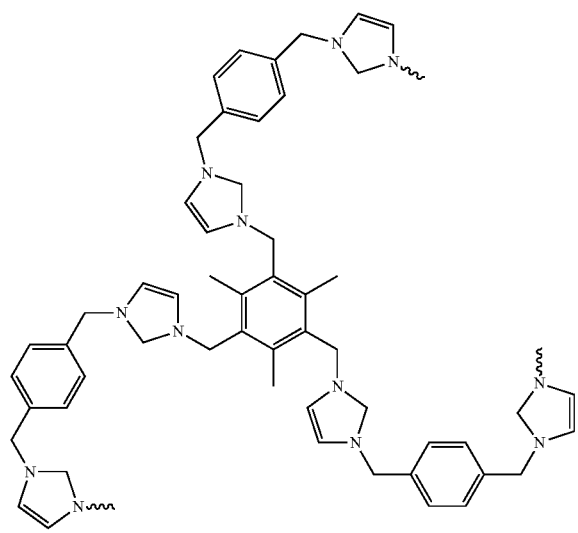

L12

The longer reaction time for the P1 catalysed reaction may be due to the heterogeneous reaction behavior in this solid catalyst system. A reaction intermediate Poly(NHC—$CO_2$)$_{0.5}$(NHC—Cu)$_{0.5}$ was synthesized by reaction of Poly(NHC)$_{0.5}$(NHC—Cu)$_{0.5}$ (P1) with $CO_2$. This intermediate was directly used to react with stoichiometric amount 1-ethynylbenzene (1 eq. to NHC—$CO_2$) under standard condition without an additional $CO_2$ source. 52% yield of phenylpropiolic acid was obtained in 24 hours. With these experiment results, it is believe that the unique structure of P1 catalyst is the key to the high activities. The free carbene species in the structure are randomly located around copper center and act as an organo catalyst to activate $CO_2$. This essential step may reduce the activation energy barrier for $CO_2$ insertion.

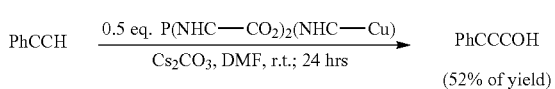

(52% of yield)

The catalytic system is not sensitive to a variety of functional groups, such as —COOR, —OH, —CHO, —CN, —$NO_2$ etc. It provides a powerful tool for synthesis of highly functionalized propiolic acids for the first time.

It is known that copper acetylide is the key intermediate for copper catalyzed C—H activation of terminal alkynes reactions and the Cu—C bond is active for $CO_2$ insertion. A possible catalytic cycle for copper catalyzed carboxylation of terminal alkynes with $CO_2$ is proposed as shown in Scheme 4.

Scheme 4. Proposed catalytic cycle.

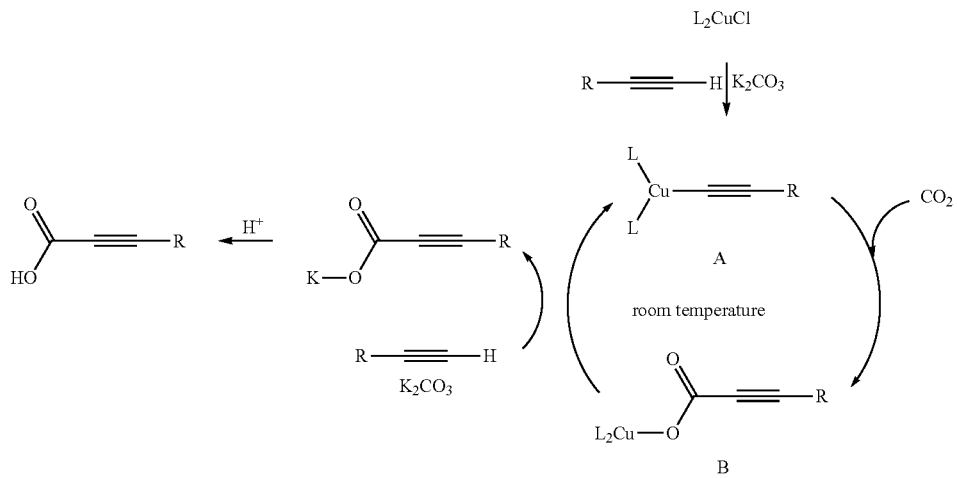

It is thought that copper acetylide intermediate A forms from the reaction of terminal alkyne and $L_2CuCl$ in the presence of base. Subsequent $CO_2$ insertion into the polar Cu—C bond will form propynoate intermediate B, in which it will undergo metathesis with base in the system. This would release potassium propynoate and regenerate active copper(I) species that will then quickly react with terminal alkyne to form intermediate A. This is the first catalytic cycle to generate simple carboxylate products without using organometallic transmetallation reagents. However, it must be noted that the copper propynoate intermediate B is not stable at elevated temperatures. In general, raising reaction temperatures will promote or speed up the reaction. However, in this reaction, intermediate B may decompose over heat to re-form A through de-carboxylation process, Scheme 5.

In summary, the inventors have successfully developed a copper catalyzed transformation of $CO_2$ to carboxylic acid through C—H bond activation and carboxylation of terminal alkynes. The direct C—H bond functionalization was also achieved with $Cs_2CO_3$ as the base and in the absence of transition metal catalyst. Various propiolic acids were synthesized in good to excellent yields under ambient conditions without consumption of any organometallic or organic reagent additives. The most remarkable advantage of this mild reaction system is its tolerance towards a wide substrate scope. The catalytic system is active to both aryl and alkyl alkynes, but not sensitive to variety functional groups, such as COOH, OH, CHO etc. This opens up access to a range of highly functionalized propiolic acids for the first time. In addition, this simple and economical protocol is easy to scale Scheme 5

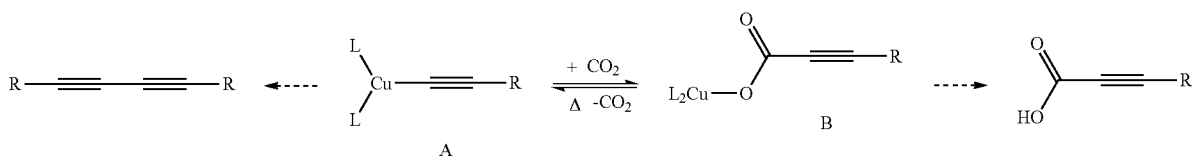

As the temperature was raised from ambient temperature (25° C.) to 60° C. for the reaction of 1a, the yield of 1b was dropped from 90% to 42%. Instead, some homo-coupling byproduct 1c was observed. Under room temperature condition, due to the quick insertion of $CO_2$ into intermediate A and also the shortage of oxidant, production of 1c is prohibited. At elevated temperature, intermediate B decompose to A and $CO_2$ may also act as an oxidant for the producing 1c. The same reaction conducted at 0° C. showed lower activity but high selectivity. This observation is well in agreement with the proposed hypothesis. The calculated free energy profile (DFT, B3LYP/6-31G level) showed that the overall reaction is an exothermic process with a small negative energy difference $\Delta E=-26.1$ kcal/mol for the carboxylation of 1-ethynyl-benzene.

$$PhCCH + CO_2 + K_2CO_3 \rightarrow PhCCCOOK + KHCO_3 \; \Delta E = -26.1 \text{ kcal/mol} \quad (1)$$

up and has potential for practical application. In addition, the Poly-NHC—Cu system demonstrates a new concept for the cooperative effect of organo and organometallic catalysts.

Using the process of the present invention, various propiolic acids may be synthesized in good to excellent yields under ambient conditions without the consumption of any organometallic or organic reagent or additive. A significant advantage of the present mild reaction system is its wide scope of substrate tolerance. The catalytic system is active towards both aryl and alkyl alkynes, and is not sensitive to a variety functional groups, such as $NO_2$, OH, CN, CHO. In addition, the process is simple, relatively inexpensive and easy to scale up. It therefore has great potential for practical applications.

Advantages of the Present Technology:
1. Successful with 13 types of terminal alkynes using $K_2CO_3$ with 80-91% yield of propiolic acid of reaction time 16-24 hrs 2. Catalytic system is not sensitive to type and position of benzene ring substitutions (p-,m-,o- all similar % yield)
3. Successful with 6 terminal alkyl alkynes with $Cs_2CO_3$ as base with 80-91% yield of Propiolic acid of reaction time 24 hrs
4. Catalytic system is not sensitive to a variety of functional groups (—OH alcohol/—COOH carboxylic acid/—CHO Aldehyde)
5. No net consumption of any organometallic or organic reagent additives.

EXAMPLES

General Information: All solvents are anhydrous and bought from Sigma-Aldrich® (99.8%). The alkynes were used without purification from commercial suppliers, unless otherwise indicated. The carbonates were all dried under vacuum with heating before use. $^1H$ and $^{13}C$ NMR spectra were recorded on Bruker® AV-400 (400 MHz) spectrometer. Chemical shifts were reported in ppm from tetramethylsilane with the solvent resonance as the internal standard. GC-MS was performed on Shimadzu® GCMS QP2010. Elemental analysis (C, H, N) was performed on EAI CE-440 Elemental Analyzer. Reactions were monitored by thin layer chromatography using 0.25-mm E. Merck® silica gel coated glass plates (60E-254) with UV light to visualize the course of reaction. All reactions were performed in oven-dried (140° C.) or flame-dried glassware under an inert atmosphere of dry $N_2$ or Ar.

Preparation of $P(NHC)_{0.5}(NHC—Cu)_{0.5}$. $NaO^tBu$ (60 mg, 0.6 mmol) was added to a DMF (10 ml) suspension of Polyimidazolium[1] (250 mg) in a reaction flask. The reaction mixture was stirred for 1 h, and then CuCl (25 mg, 0.25 mmol) was added. The resulting mixture was stirred at 80° C. for 6 h. The solid product was filtered and dried to obtain a pale-yellow powder $P(NHC)_{0.5}(NHC—Cu)_{0.5}$. The catalyst is directly used for reaction. The co-existence of metal center and free carbene was studied in reference General Procedure for Carboxylation of the Terminal Alkynes (1b as Example) CuCl (4.0 mg, 0.04 mmol, 2.0 mol %), TMEDA (3.5 mg, 0.03 mmol, 1.5 mol %), and $K_2CO_3$ or $Cs_2CO_3$ (2.4 mmol) were added to the DMF (4 mL) in the reaction tube (10 mL). $CO_2$ and 2 mmol of terminal alkynes (1a, 204 mg) were introduced into the reaction mixture under stirring. The reaction mixture was stirred at room temperature (about 24° C.) for 16 hours. After completion of the reaction, the reaction mixture was transferred to the potassium carbonate solution (2 N, 5 mL) and the mixture was stirred for 30 mins. The mixture was extracted with dichloromethane (3×5 mL) and the aqueous layer was acidified with concentrated HCl to PH=1, then extracted with diethyl ether (3×5 mL) again. The combined organic layers were dried with anhydrous $Na_2SO_4$, filtered and the solution was concentrated in vacuum affording pure product. Element analysis calcd (%) for 1b [$C_9H_6O_2$ (146.0)]: C, 73.97; H, 4.14. found: C, 73.82; H, 4.07. Data for $^1H$ and $^{13}C$ NMR of acids were all conducted in $d_6$-DMSO or $CDCl_3$ and consistent with the data in reported literatures.

Typical Procedure for Methylation of Propiolic Acid with Iodomethane (1b as Example) $CH_3I$ (2.2 mmol) and $K_2CO_3$ (2.2 mmol) were added to the solution of Propiolic acid (1b, 2 mmol) in acetonitrile and the obtained mixture was stirred at room temperature. The reaction was monitored by TLC until the starting 1b disappeared. After 3 hours, the mixture was extracted with ether (3×5 mL). The combined ether part was purified by column chromatography on silica gel (dichloromethane:hexane=1:3) to give pure methyl 3-phenylpropiolate in 98% yield. GC/Ms: m/z: 160. Data for $^1H$ and $^{13}C$ NMR of methyl 3-phenylpropiolate was conducted in $CDCl_3$ and consistent with the data in reported literature.

Calculation Method:

The density functional theory (DFT) calculations were carried out with the Gaussian 03 software. The exchange-correlation functional employed is dubbed Becke, three-parameter, Lee-Yang-Parr (B3LYP) which includes a fraction of Hartree-Fock exchange to reduce the self-interaction error. In this study, the 6-31(G) basis sets were used. After fully optimized the structure of each compound, its total energy was obtained. For each reaction, the stationary structures were obtained by optimizing the complex structures along the intrinsic reaction coordinate of the reaction pathway.

The invention claimed is:

1. A process for converting a terminal alkyne into an alkynoic acid comprising exposing the alkyne to carbon dioxide in the presence of a copper(I) species, a base and a complexing agent capable of complexing copper(I).

2. The process of claim 1 wherein the copper(I) species is copper (I) chloride.

3. The process of claim 1 wherein the copper(I) species is present in catalytic amount relative to the alkyne.

4. The process of claim 1 wherein the base is a basic salt.

5. The process of claim 1 wherein the base is present at a concentration of at least 10 mol% of the alkyne.

6. The process of claim 1 wherein the complexing agent is an organic nitrogen species.

7. The process of claim 6 wherein the organic nitrogen species has at least two nitrogen atoms per molecule.

8. The process of claim 7 wherein the organic nitrogen species is a diaminoalkane.

9. The process of claim 6 wherein the complexing agent is an N-heterocyclic carbene.

10. The process of claim 9 wherein the N-heterocyclic carbene is a polyimidazolium.

11. The process of claim 9 wherein the copper(I) species and the complexing agent are in the same molecule, whereby said complexing agent is a poly-N-heterocyclic carbene in which at least some carbene centres are complexed with copper(I).

12. The process of claim 11 wherein at least some carbene centres are not complexed with copper(I), said process comprising the step of complexing the carbon dioxide with the complexing agent to form a polymeric reagent comprising a poly-N-heterocyclic carbene in which some carbene centres are complexed with copper(I) and other carbene centres are complexed with carbon dioxide, said step being conducted before exposing the alkyne to said polymeric reagent.

13. The process of claim 1 wherein the complexing agent is present in a catalytic amount.

14. The process of claim 1 wherein the partial pressure of carbon dioxide over the reaction is 1 atmosphere or less.

15. The process of claim 1 wherein the alkyne is a 2-phenylalkyne.

16. The process of claim 1 wherein the akyne has a $NO_2$, OH, CN, CHO or COOH group or more than one of these.

17. A process for converting a terminal alkyne into an alkynoic acid comprising exposing the alkyne to carbon dioxide in the presence of a carbonate salt at a temperature of at least 60° C. and a partial pressure of carbon dioxide of at least 1 atmosphere.

18. The process of claim 17 wherein the carbonate salt is present in equimolar or greater amount relative to the alkyne.

19. The process of claim 17 wherein the partial pressure of carbon dioxide over the reaction is at least 2 atmospheres.

20. A process for converting a terminal alkyne into an alkynoic acid comprising exposing the alkyne to carbon dioxide in the presence of a carbonate salt at a temperature of at least 60° C. and a partial pressure of carbon dioxide of at least 1 atmosphere, and wherein the alkyne is a 2-phenylalkyne.

* * * * *